United States Patent [19]

Lax

[11] Patent Number: 5,976,127
[45] Date of Patent: Nov. 2, 1999

[54] SOFT TISSUE FIXATION DEVICES

[76] Inventor: Ronald Lax, 2740 SW Martin Downs Suite 300, Palm City, Fla. 34990

[21] Appl. No.: 09/007,246

[22] Filed: Jan. 14, 1998

[51] Int. Cl.$^6$ .................................................. A61B 17/36
[52] U.S. Cl. ................................ 606/32; 606/41; 606/232
[58] Field of Search ........................... 606/27–32, 45–50, 606/213, 8, 151, 232; 607/113, 151, 153, 99, 101–102

[56] References Cited

U.S. PATENT DOCUMENTS

| | | |
|---|---|---|
| 4,705,040 | 11/1987 | Mueller et al. . |
| 5,207,670 | 5/1993 | Sinofsky . |
| 5,395,391 | 3/1995 | Essig et al. ............................ 606/220 |
| 5,458,596 | 10/1995 | Lax et al. . |
| 5,514,130 | 5/1996 | Baker . |
| 5,569,239 | 10/1996 | Sinofsky . |
| 5,569,242 | 10/1996 | Lax et al. . |
| 5,669,934 | 9/1997 | Sawyer . |
| 5,690,676 | 11/1997 | DiPoto et al. . |
| 5,810,810 | 9/1998 | Tay et al. .................................. 606/50 |
| 5,827,298 | 10/1998 | Hart et al. .............................. 606/139 |

*Primary Examiner*—Linda C. M. Dvorak
*Assistant Examiner*—Roy Gibson
*Attorney, Agent, or Firm*—Pennie & Edmonds LLP

[57] ABSTRACT

A surgical instrument for repairing a lesion, in particular during arthroscopic procedures, in which the lesion is closed by a chemical and for physical repair is preferably a bioabsorbable tubular member placed across a lesion and irradiated with RF energy. The repair member is placed via a trocar delivery device. The repair system disclosed herein is easily usable for arthroscopic procedures.

10 Claims, 5 Drawing Sheets

SOFT TISSUE FIXATION DEVICES

FIELD OF THE INVENTION

The present invention relates to surgical instruments and more particularly, surgical instruments for repairing soft tissues wherein the instrument inserts a bioabsorbable member across a lesion to repaired and by causing tissue on opposite sides of the lesion to be drawn together.

BACKGROUND OF THE INVENTION

Numerous surgical instruments for the suturing of human or animal tissues by physically or chemically attaching the tissue to the suture material are known in the art. For example, U.S. Pat. No. 5,569,239 to Sinofsky and U.S. Pat. No. 5,669,934 to Sawyer both disclose examples of laying down a layer of energy reactive adhesive material along the incision and closing the incision by applying energy (either optical or RF energy) to the adhesive and surrounding tissue. The applied energy denatures the filler material and adjacent biological tissue. The reaction occurs to different degrees depending on the type, amount and intensity of energy applied. The denatured tissue and filler mix and when cooled harden to essentially glue the tissue together. Drawbacks to the disclosed methods include the need to physically place the adhesive material on the wound site, the cumbersome and thus inaccurate direction of the energy beam, both disclosures require that the surgeon manipulate several instruments to accomplish the task including physically holding the tissue in place and neither of patented devices or methods that may be readily used during arthroscopic procedures, such as meniscus repair.

It also known in the art that it may be desirable to mechanically attach the tissue to an anchor wherein the anchor is attached to "thread-type" sutures which are then used to sew up the incision such as disclosed in U.S. Pat. No. 5,690,676. There is also the conventional approach to joining tissue segments by employing mechanical sutures or staples. This suffers from the draw back that use of conventional sutures may leave gaps between stitches and requires several steps to complete a stitch. Additionally both conventional staples and sutures do not chemically bind or mechanically attach to the tissue, thus they may move about or slip.

There remains a need in the art for a less complex, and more precise instrument for binding or securing together incisions or injured tissue in a variety of surgical procedures, particularly in arthroscopic procedures.

SUMMARY OF THE INVENTION

It is therefore an object of the present invention to provide a single device that a surgeon may use to close a lesion in a tissue. It is a further object of the present invention to provide a device that will close the lesion by using a physical and chemical suture. It is yet a further object of the invention to provide a device to close a lesion by use of a pure physical suture wherein the tissue is attached to the suture.

This and other objectives are achieved according to the present invention by a device having a body portion with a distal tip, a shaft portion slidingly disposed within the body portion and the distal tip, and a mechanism to hold the lesion together after the device is removed from the sutured site.

DETAILED DESCRIPTION OF THE INVENTION

Figure 1:
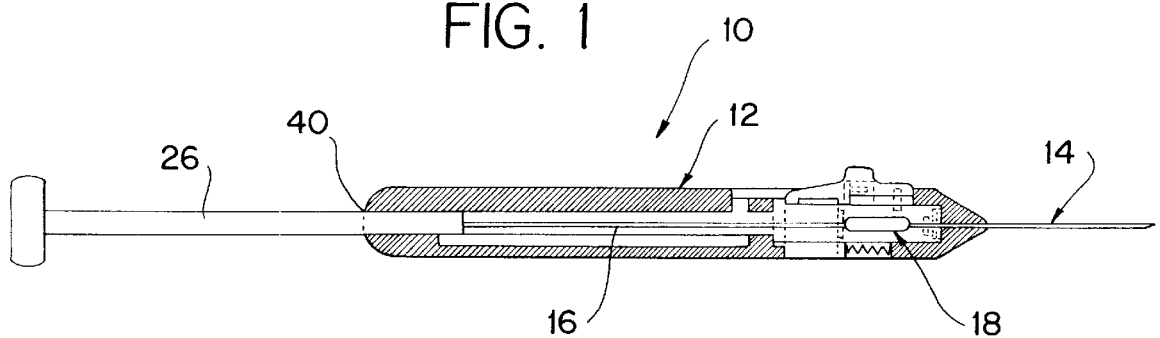
FIG. 1 is a partial cross-sectional view of a surgical instrument according to the present invention.
Figure 2:
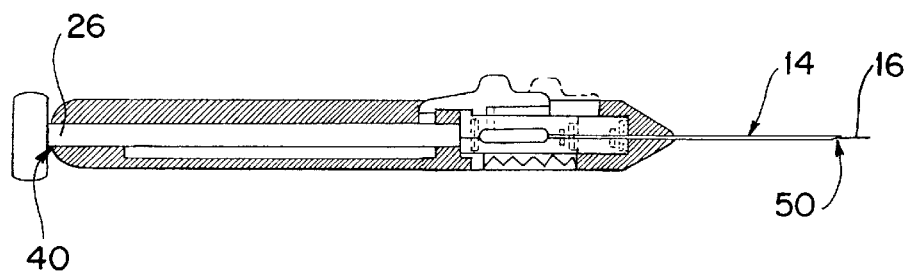
FIG. 2 is a partial cross-sectional view of the surgical instrument shown in FIG. 1 with the shaft portion protruding out of the distal opening.

As shown in FIGS. 1 and 2, surgical instrument 10, according to a first preferred embodiment of the present invention, includes body portion 12 with distal tip 14, shaft portion 16 slidingly disposed within body portion 12 and distal tip 14, and repair member 18A (shown in FIG. 4) to secure together opposite sides of a soft tissue lesion.

Figure 3:
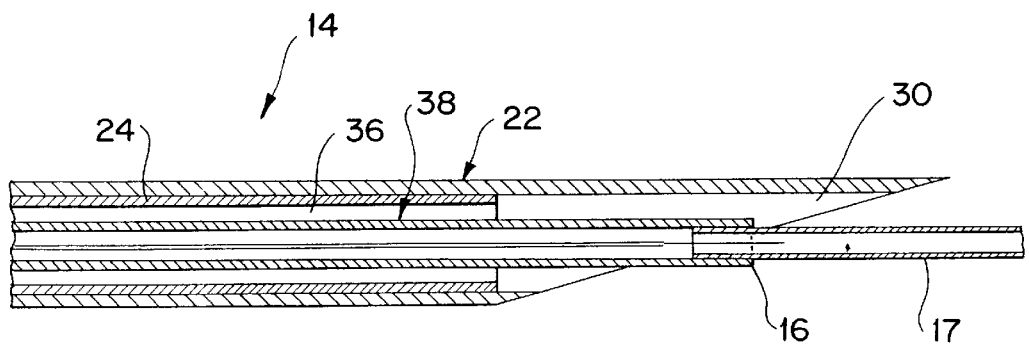
FIG. 3 is a partial cross-sectional view of the distal tip according to a first preferred embodiment of the present invention.
Figure 5A:
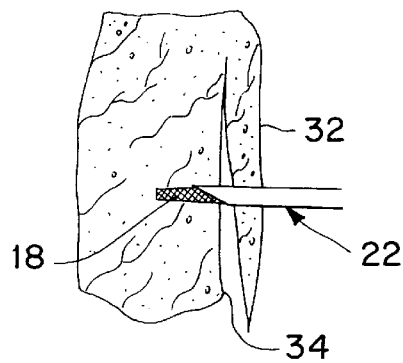
FIGS. 5A–5C depicts a cross-section of a lesion undergoing repair according to a preferred embodiment of the present invention.
Figure 5B:
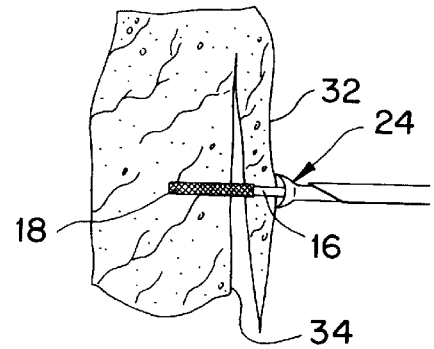
Figure 5C:
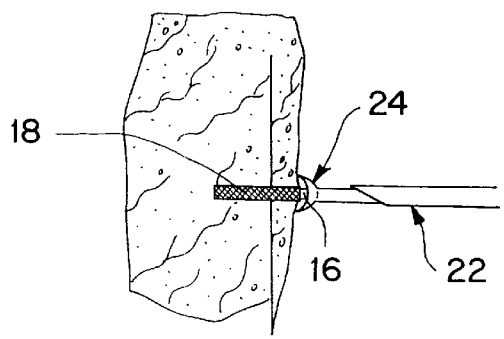
Figure 5D:
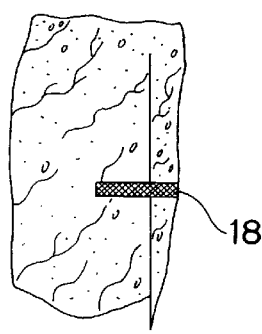

Turning to FIG. 3, distal tip 14 comprises outer sleeve 22 with a distal opening, preferably a standard canula or trocar with a needlelike distal end, attached to and in communication with body portion 12. Inner sleeve 24 is slidingly disposed within outer sleeve 22 and extends through the distal end of and into body portion 12. Shaft portion 16 is slidingly disposed within inner sleeve 24 and is attached to plunger rod 26 at the proximal end of body portion 12 such that axial movement of plunger rod 26 correspondingly slides shaft portion 16 within the inner sleeve. Independent of shaft portion 16, inner sleeve 24 may be slid distally to extend out of distal end 30 of outer sleeve 22. In an alternative embodiment, the distal end of inner sleeve 24 may be designed to flare outwards when pushed beyond distal opening 30 of outer sleeve 22 (best depicted in FIGS. 5B & 5C) which, as will be discussed shortly, aids in forcing the opposite sides of the lesion together. Annular channel 36 is defined between inner sleeve 24 and shaft 16 and provides fluid communication to distal end 30.

Shaft portion 16 preferably comprises an RF probe, with distal end 17 formed as a mandrel and adapted to deliver radio frequency energy to surrounding tissue when placed therein. The basic features of such probes for the delivery of RF energy and surgical procedures are known in the art as described, for example, in U.S. Pat. No. 5,569,242 and U.S. Pat. No. 5,514,130, each of which is incorporated by reference here in its entirety. As explained below, distal mandrel 17 is shaped to carry and deliver repair to number 18.

Figure 4A:
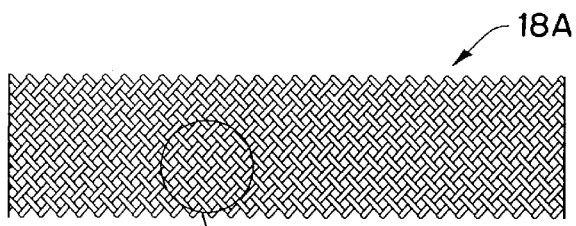
FIG. 4 schematically depicts a tubular member formed from woven bioabsorbable fibers according to one embodiment of the present invention.
Figure 4B:
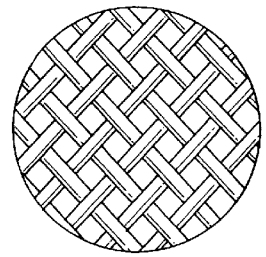

Repair member 18A is generally a hollow tubular member, as shown in FIG. 4, manufactured from a biosorbable from material which is relatively inert when exposed to RF energy. Member 18A is preferably woven tube made from fibers of bioabsorable material such as various polylactide polymers that are commercially availabel as absorbable suture material. Member 18 is disposed over RF probe mandrel 17, which is disposed within inner sleeve 24, which is in turn disposed within trocar 22.

In order to repair a soft tissue lesion, for example, a torn meniseus, as shown in FIGS. 5A–5D, trocar is inserted through top flap 32 in the tissue to be repaired and into bottom flap 34. Trocar 22 is then withdrawn, leaving probe 16 with member 18 on mandrel 17 in place as in FIG. 5A. Inner sleeve 24 is then advanced out of trocar 22. Inner sleeve 24 is advanced further causing its distal end to abut the surface of tissue flap 32 and force tissue flaps 32 and 34 together (best depicted in FIG. 5B & 5C). RF energy is applied to the tissue surrounding repair member 18 via mandrel 17 of probe 16 in a controlled manner to cause the surrounding tissue to shrink and be drawn together around member 18, thus closing the lesion. Such tissue shrinkage via controlled application of RF energy is described for example in U.S. Pat. No. 5,458,596, which is incorporated by reference herein.

Member 18 serves as an integral fastener holding together flaps 32 and 34, while natural healing processes occur. The interstices between the briefed fibers enhance this fastening function by receiving tissue therein.

Application of RF energy also causes tissue proteins to denature and form an adhesive like substance. RF probe 16 is removed leaving behind member 18 to which the denatured proteins adhere as they begin to cool down. In an alternative embodiment, annular channel 36 may be used to deliver a fluid that forms an adhesive after being exposed to RF energy. Additionally, the preferred composition of member 18, absorbable suture materials, such as polyglactin fibers and the like, when subject to RF energy, also forms an adhesive-like substance in addition to the denaturing proteins of the surrounding tissue. Thus, a stronger adhesive bond will form between the surrounding tissue and mechanism 18 which results in a better suture. Furthermore, the materials used in this embodiment are entirely bioabsorbable allowing the body to heal itself and then digest the suture.

Figure 6A:
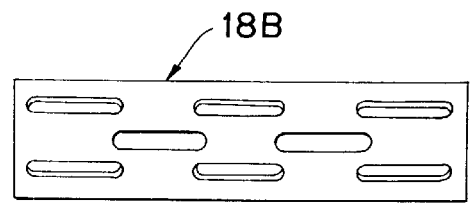
FIGS. 6A-6B schematically depicts an alternative tubular member formed from extruded bioabsorbable fibers according to an alternative preferred embodiment of the present invention.
Figure 6B:
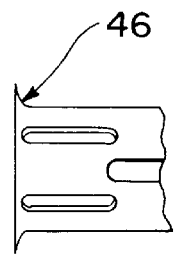
Figure 7A:
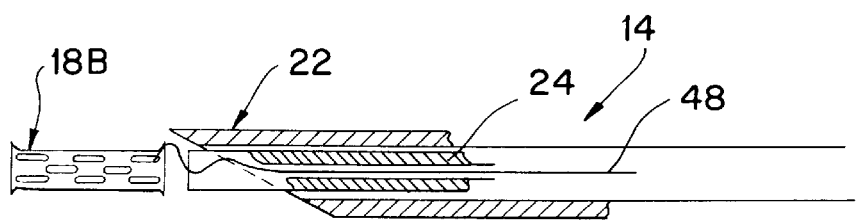
FIGS. 7A-7B are a partial cross-section and a partial side view, respectively, of the distal tip according to an alternative preferred embodiment of the present invention.
Figure 7B:
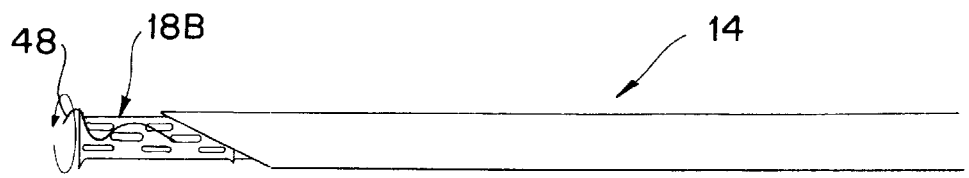
Figure 8:
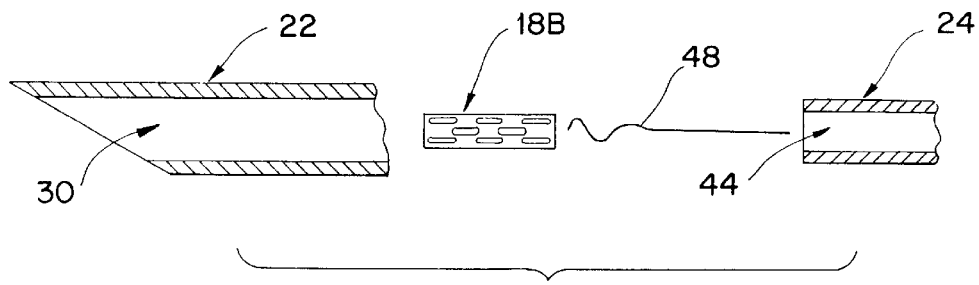
FIG. 8 is a partial, cross-sectional, exploded view of the preferred embodiment depicted in FIGS. 7A and B.
Figure 9:
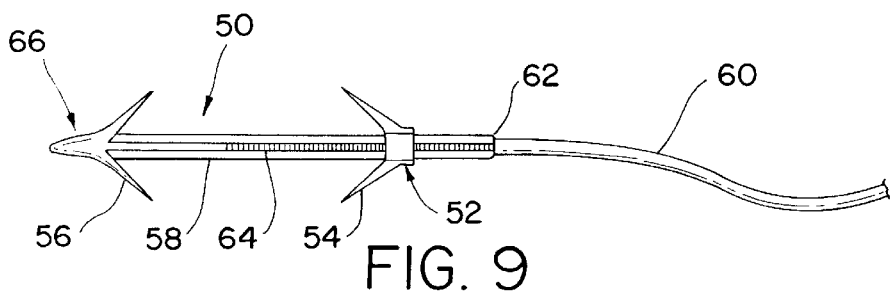
FIG. 9 is a side view of an anchor according to a further preferred embodiment of the present invention.
Figure 10A:
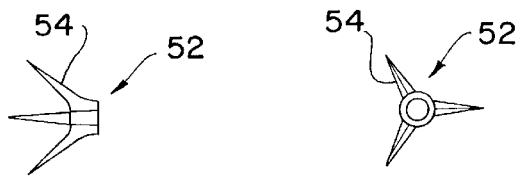
FIGS. 10A and B depict plan and side views, respectively of a sliding member in the embodiment of the present invention depicted in FIG. 9.
Figure 10B:
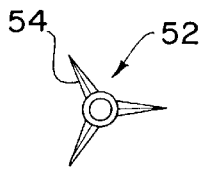

An alternative preferred embodiment, depicted in FIGS. 6–8, is similar to the first two preferred embodiments except as described below. In this embodiment, the RF probe 16 comprises shaped wire 48 which can be quickly heated and deliver RF energy. Wire/RF-probe 48 is disposed through center lumen 44 of inner sleeve 24. Center lumen 44, passing through inner sleeve 24 places distal end 30 in fluid communication with proximal end 40 of body portion 12.

In an alternative embodiment shown in FIGS. 6A and 6B, repair member 18B has a tubular shape as before, but is an extruded biocompatible absorbable material, such as polyglactin and the like, rather than braided fibers. Openings 19 are provided for tissue engagement and to permit fluid flow which facillitates the healing process.

As with the prior embodiment, member 18B is disposed within trocar 22 and abuts inner sleeve 24. Member 18B and inner sleeve 24 are dimensioned such that the distal end of inner sleeve 24 will abut the proximal end of member 18B. Therefore advancement of inner sleeve 24 will advance member 18B as well. However, inner sleeve 24 only abuts repair member 18B therefore, withdrawal of inner sleeve 24 will not correspondingly withdrawal member 18B. Also, as before, repair member 18B is placed across a lesion by inserting trocar 22 through the tissue to position member 18B at the site of repair. Inner sleeve 24 is advanced as trocar 22 is correspondingly withdrawn. This latter configuration leaves member 18B disposed within the tissue across lesion with wire/RF-probe 48 disposed down its center as depicted in FIG. 7B. Wire/RF-probe 48 is quickly heated and simultaneously rotated to form flange 46 (best depicted in FIG. 6B) by softening and deforming the distal end of mechanism 18. Flange 46 assists in holding member 18B in place. Flanges 46 may be similarly formed at each end of member 18B if desired. RF energy is applied via wire/RF-probe 48 in a similar fashion as described above and with similar results. The apparatus is removed from the lesion leaving only mechanism 18B in place as described above.

FIGS. 9–12, illustrate a further preferred embodiment of the present invention. In this embodiment, the apparatus also includes body portion 12 with distal tip 14. Distal tip 14 comprises trocar 22 with a distal opening, attached to and in communication with body portion 12. Inner sleeve 24 is slidingly disposed within outer sleeve 22 and extends through the distal end of and into body portion 12 (best depicted in FIGS. 11 & 12). Anchor 50 is manufactured by extruding and shaping the end of fibrous absorbable suture material 60 such that anchor 50 formed with distal end 66 and shaft 58, relatively rigid with relatively flexible suture material 60 remaining attached to proximal end 62 of rigid anchor 50.

Figure 11:
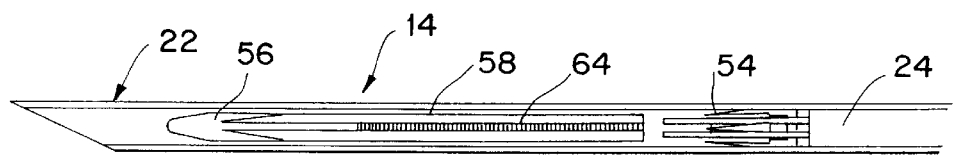
FIG. 11 is a partial cross-sectional, exploded view of the distal tip for the embodiment of the present invention depicted in FIGS. 9-10.
Figure 12:
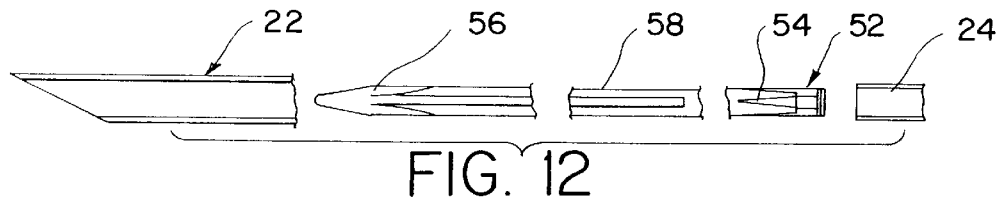
FIG. 12 is a partial cross-sectional, exploded view of the embodiment depicted in FIGS. 9–11.
Figure 13A:
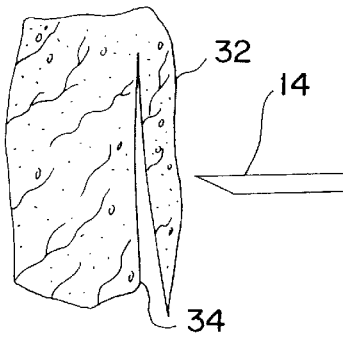
FIG. 13A–13H depicts a cross-section of a lesion undergoing repair according to an alternative embodiment of the present invention utilizing the device depicted in the FIGS. 9–12.
Figure 13B:
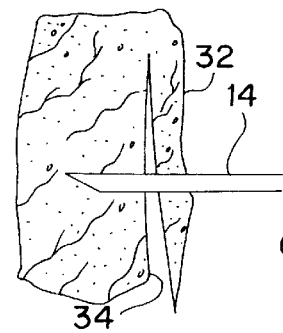
Figure 13C:
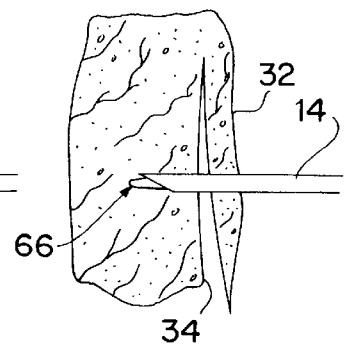
Figure 13D:
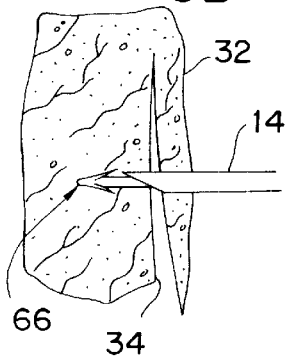
Figure 13E:
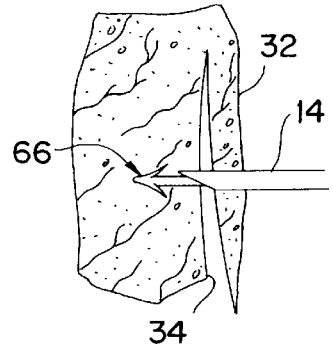
Figure 13F:
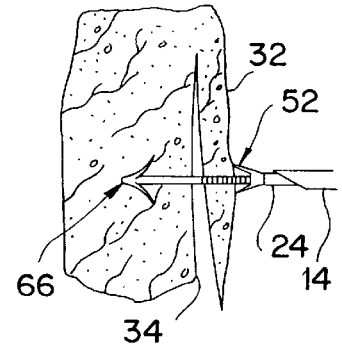
Figure 13G:
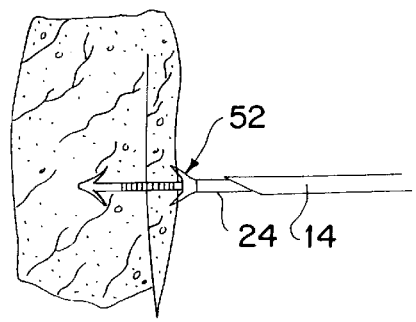
Figure 13H:
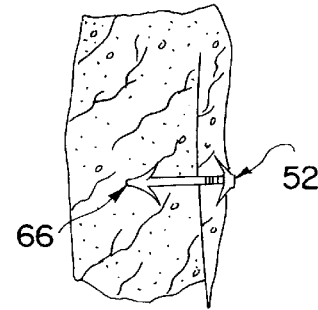

Distal end 66 of anchor 50 has at least one resiliently, and preferably a plurality of, deformable barbs 56 such that in the deformed position anchor 50 will fit inside trocar 22 as in FIG. 11. Resiliently deformable barb 56 will flare out such that barb 56 will point towards the proximal end of anchor 50. Sliding member 52 also has at least one deformable barb 54, and preferably a plurality, such that in the deformed position sliding member 52 will fit inside trocar 22 as in FIG. 11.

Sliding member 52 fits over shaft 58. Shaft 58 has a locking mechanism 64, preferably a ratchet mechanism such as found on "tie-wraps", that only allows sliding member 52 to move unidirectionally towards distal end 66 of anchor 50. It will be readily recognizable to those skilled in the art that other standard one-way locking mechanisms may be substituted for locking mechanism 64. Flexible suture material 60 passes through inner sleeve 24 towards distal end 40 of body portion 12. Flexible suture material is used to set anchor 50 after it has been inserted across lesion 20 as described below. Inner sleeve 24 is configured to about proximal end 62 of anchor 50 for the purpose of ejecting anchor 50 trocar outer sleeve 22 and for advancing sliding member 52.

In this embodiment, depicted in FIGS. 13A–13H, trocar 22 is inserted across a lesion and inner sleeve 24 advances the distal and 66 of anchor 50 into the tissue. Once distal end 66 is positioned, flexible suture 60 is tugged to set collapsible barbs 56. Inner sleeve 24 is advanced further to advance sliding member 52 towards distal end 66 and force the separate edges of the lesion to come together. Trocar 22 then is withdrawn and flexible suture 60 is trimmed leaving the bioabsorbable anchor in place.

All of the embodiments of the present invention comprise a single and easily operable device which can be manufactured in small enough sizes to be used in arthroscopic or endoscopic procedures. As should be readily apparent to those skilled in the art various modifications and adaptations of the structures and examples above described will be readily apparent, in particular, different shapes of sleeves may be used in order to accommodate different sizes or shapes of lesions, without departure from the spirit and scope of the invention, the scope of which is defined in the appended claims.

What is claimed is:

1. A surgical instrument for fixation of tissues, comprising:
  a main body portion having a sharpened distal end and a proximal end;
  a shaft portion, having distal and proximal ends, slidingly disposed within said main body portion such that the distal end of said shaft portion may extend beyond the distal end of said main body portion; and
  a repair member configured and dimensioned to be received within said main body portion and cooperate with the distal end of said shaft portion for ejection from said main body portion, said repair member having at least one end adapted for placement within biological tissue and including tissue securing means adapted to hold at least two sections of said tissue in close proximity to one another;
  wherein said shaft portion and said main body portion cooperate together to position said repair member within said tissue and activate said tissue securing means to hold together separated tissue layers.

2. The surgical instrument according to claim 1, wherein:
  a distal section of said main body portion comprises an inner sleeve and outer trocar;
  said inner sleeve is slidingly disposed within said trocar such that it may extend beyond the sharpened distal end of said trocar;
  said shaft portion is slidingly disposed within said inner sleeve such that it may extend beyond the distal end of said trocar and inner sleeve; and
  said repair member is a tubular member adapted to be received over said shaft portion and abut the distal end of said inner sleeve.

3. The surgical instrument according to claim 1, wherein said repair member comprises:
  a first rigid portion with proximal and distal ends configured to fit within said distal end of said main body portion;
  a relatively flexible and longer second portion beginning at the proximal end of said rigid portion, wherein said flexible portion forms said shaft portion; and
  a sliding attachment, disposed towards the proximal end of said rigid portion wherein said sliding attachment fits within said main body portion;
  wherein said distal end of said rigid portion has at least one barb such that when the distal end of said rigid portion exits the distal end of said main body portion said at least one barb extends towards the proximal end of said rigid portion, wherein said sliding attachment also has at least one barb configured such that when the sliding attachment exits the distal end of said main body portion said at least one barb extends towards the distal end of said rigid portion, and wherein said sliding attachment may only unidirectionally slide towards the distal end of said rigid portion.

4. The surgical instrument according to claim 3, wherein said inner sleeve is configured to abut said sliding attachment such that advancement of said inner sleeve relative to both first and second portions will unidirectionally advance said sliding attachment towards the distal end of said rigid portion.

5. The surgical instrument according to claim 4, wherein said repair member is manufactured from a bioabsorbable material.

6. The surgical instrument according to claim 2, wherein said shaft portion comprises a radio frequency probe, with said distal end of said shaft portion adapted to deliver radio frequency energy to a tissue area surrounding said repair member.

7. The surgical instrument according to claim 6 further comprising an annular fluid supply channel defined by said trocar and inner sleeve, and wherein said annular channel places the proximal and distal ends of said main body portion in fluid communication.

8. A method for repairing separations of soft tissue, comprising
  inserting a cannula into the tissue, across the separation;
  delivering an individual, elongated repair member to said separation through said cannula;
  positioning said repair member across said separation;
  drawing tissue together on both sides of the separation; and
  securing the tissue with said repair member.

9. The method according to claim 8, wherein said drawing step comprises applying force to said tissue with a sleeve slideable in said canula and by shrinking tissue through controlled application of RF energy.

10. The method according to claim 9 wherein said repair member is a bioabsorbable tube with a plurality of side holes therein.

* * * * *